United States Patent [19]

Lemons

[11] Patent Number: 5,273,964
[45] Date of Patent: Dec. 28, 1993

[54] INORGANIC AND ORGANIC COMPOSITION FOR TREATMENT OF BONE LESIONS

[76] Inventor: J. E. Lemons, c/o University of Alabama in Birmingham, School of Dentistry, Box 49, Birmingham, Ala. 35294

[21] Appl. No.: 280,949

[22] Filed: Dec. 7, 1988

Related U.S. Application Data

[63] Continuation of Ser. No. 946,432, Dec. 23, 1986, abandoned, which is a continuation of Ser. No. 713,768, Mar. 20, 1985, abandoned.

[51] Int. Cl.$^5$ .................. A61K 37/02; A61K 33/42
[52] U.S. Cl. ............................ 514/2; 514/21; 514/802; 424/602; 530/356; 128/DIG. 8; 607/94
[58] Field of Search ............... 514/2, 21, 801; 424/602; 530/356; 128/92 YG, DIG. 8

[56] References Cited

U.S. PATENT DOCUMENTS

| | | | |
|---|---|---|---|
| 3,649,347 | 3/1972 | Battista | 424/36 |
| 4,097,935 | 7/1978 | Jarcho | 128/92 C |
| 4,440,750 | 4/1984 | Glowacki et al. | 424/95 |

*Primary Examiner*—Jacqueline Stone

[57] ABSTRACT

A method for the treatment of bone lesions or bone deficiencies in a living mammal comprising administering a composition comprising an inorganic phase and an organic phase wherein the inorganic phase comprises a porous particulate TCP ceramic or a nonporous or microporous particulate HAP ceramic or a mixture of porous particulate TCP ceramic and nonporous or microporous particulate HAP ceramic, wherein the organic phase comprises a purified hydrated collagen product which is mixed with and forms a continuous or substantially continuous surface coating over said inorganic phase(s) and a hydrated collagen-demineralized bone product which is mixed with and forms a substantially continuous surface coating over said purified hydrated collagen product surface coating or the organic phase comprises a hydrated collagen-demineralized bone product which is mixed with and forms a continuous or substantially continuous surface coating over said inorganic phase and a purified hydrated collagen product which is mixed with and forms a continuous or substantially continuous surface coating over said hydrated collagen-demineralized bone product surface coating. The composition may be administered at surgical reconstruction or delivered to the lesion site by syringe.

24 Claims, No Drawings

INORGANIC AND ORGANIC COMPOSITION FOR TREATMENT OF BONE LESIONS

This is a continuation of application Ser. No. 946,432 filed Dec. 23, 1986, the disclosure of which is incorporated herein by reference, now abandoned, which is a continuation of application Ser. No. 713,768, filed Mar. 20, 1985, now abandoned.

BACKGROUND OF THE INVENTION

1. Field of the Invention

This invention is drawn to a method of treating bone lesions and a composition comprised of a new combination of known substances which provide space filling, interfacial bonding of the ceramic and bone and the improved osteogenic, osteoinductive and osteoconductive properties of the organic substances placed with and onto the surfaces of the ceramic compounds. Specifically, the composition comprises an inorganic phase and organic phase wherein the inorganic phase comprises porous particulate tricalcium phosphate (hereinafter TCP) ceramic or a nonporous or microporous particulate hydroxylapatite (hereinafter HAP) ceramic or a mixture of porous particulate TCP ceramic and nonporous or microporous particulate HAP, wherein the organic phase comprises a purified hydrated collagen product which is mixed with and forms a continuous or substantially continuous surface coating over said inorganic phase and a hydrated collagen-demineralized bone product which is mixed with and forms a continuous or substantially continuous surface coating over said purified hydrated collagen product surface coating or the organic phase comprises a hydrated collagen-demineralized bone product which is mixed with and forms a continuous or substantially continuous surface coating over said inorganic phase and a purified hydrated collagen product which is mixed with and forms a continuous or substantially continuous surface coating over said hydrated collagen-demineralized bone product surface coating. The composition may be applied at surgical reconstruction or delivered to the lesion site by a syringe injection.

2. Description of the Prior Art

The medical community at large has utilized a large variety of metals, alloys, ceramics, carbons, polymers, tissue products and externally applied techniques such as electrical stimulation for the treatment of bone lesions. Metals and alloys have, for the most part, included iron, cobalt and titanium based systems. The ceramics include aluminum oxide, hydroxylapatites, calcium sulfates, zirconium oxides, calcium phosphates and other selected compounds. The carbons have been vitreous (polycrystalline glassy carbon) and the pyrolytic carbon-silicon compounds. The polymers, recently utilized, have emphasized the ultra-high molecular weight polyethylene, polysulfone, polytetrafluoroethylene, silicon rubbers, and polyesters.

The tissue product most often used for the treatment of bone lesions is autogenous bone surgically removed from the host and placed at the defect site. Both homologous and heterogeneous bone products for example, bovine bone morphogenetic protein (BMP), bovine inorganic bone, human bank bone, etc., are also used for selected treatments. Many hospitals and clinics now maintain bone bank (storage) facilities.

Numerous attempts have been made to replace the autogenous bone used in surgical procedures by inorganic biomaterials, artificial bone, metals, alloys and polymers, etc., especially in non-unions and major segmental defects. However, only limited success has been achieved.

The implantation of TCP rods in prepared segmental bone replacements and non-union correction resulted in scattered data and therefore unpredictable healing. Even where the TCP implant for non-union correction was accompanied by direct current electrical stimulation, only a very low probability for re-establishment of a bony union resulted. It was established, however, that porous TCP ceramic can serve as a scaffold with bone proliferation through the large interconnecting pores. Lemons, J. E., *Response of Combined Electrical Stimulation and Biodegradable Ceramic*, Annual Report 2, USAMRDS Contract DAMD17-75-C-5044, 1976.

A later study utilized autogenous bone and porous TCP ceramic rod, porous TCP rod or granular form TCP alone and a mixture of autogenous bone and granular porous TCP ceramic. This study indicated that the porous TCP rod alone for non-union correction was unacceptable as only two of twenty procedures obtained a bony union. The granular form alone showed incomplete healing at six weeks. The use of the rod form of porous TCP with autogenous bone was much better, with ten of twelve procedures establishing clinical union. The use of granular porous TCP ceramic and autogenous bone implant (50-50) showed clinical union at six weeks. Lemons, J. E., *Response of Combined Electrical Stimulation and Biodegradable Ceramic*, Annual Report 3, USAMRDS Contract DAMD17-85-C-5044, 1978.

In a 1979 study, the treatment of segmental eight mm lesions with granular porous TCP ceramic alone failed to heal after six weeks. However, when granular porous TCP ceramic was mixed with autogenous bone, some bridging occurred in six weeks. The best implant material was autogenous bone which showed good bridging in four weeks. When non-union correction was attempted, bridging occurred in only three of eight for the granular ceramic implant and only two of six for a 50/50 (ceramic-autogenous bone). Total autogenous bone showed a clinical union in six of seven procedures. Lemons, J. E., *Response of Combined Electrical Stimulation and Biodegradable Ceramic*, Annual Report 3, USAMRDS Contract DAMD17-85-C-5044, 1979.

In a 1981 study, healing of 23 of 25 eight mm tibial lesions, when implanted with granular (1, 2 or 3 mm average size) porous TCP ceramic mixed with equal weights of autogenous bone. However, the rod form and the granular form implants alone, while showing good biocompatability, failed to establish the same success. Lemons, J. E., *Response of Combined Electrical Stimulation and Applied Laboratory and Clinical Studies on Biodegradable Ceramic*, Annual Report, USAMRDS Contracts DAMD17-75-C5044 and DAMD17-79-C-9173, 1981.

In March 1982 a mixture comprising the granular form TCP ($-40+100$ mesh) and calcium hydroxylapatite (14 mesh) ceramic was mixed with autogenous bone and placed in a 8 mm length segmental rabbit tibial lesion. The mixture comprised equal amounts of TCP and hydroxylapatite and 50% autogenous bone. The tricalcium phosphate and hydroxylapatite granular form ceramics show good biocompatability. The hydroxylapatite is available from Sterling Winthrop Research Institute under the trademark "DURAPATITE". The combination of granular TCP ceramic and hydroxylapatite ceramic with 50% autogenous bone showed a healing of the 8 mm length segmental rabbit tibial lesion in 11 of the 12 procedures. Lemons, J. E., *Applied Laboratory and Clinical Studies on Biodegradable Ceramic*, USAMRDS Contract DAMD17-79-C-9173, 1982.

In a June 1982 study rod form porous TCP ceramic implanted at non-union sites, showed only 2 of 20 obtained a bony union. A combination of rod form porous TCP and autogeneous bone showed clinical union for 10 of 12 procedures. Electrical stimulation did not appear to greatly influence tissue ingrowth and biodegradation rates for porous TCP ceramics implants. Mixtures of autogeneous bone with granular from ceramic and autogeneous bone alone showed the best results with bridging at 6 weeks (50-50 mixture) and 4-6 weeks, respectively, of 8 mm length lesions. For total ceramic implants 14-16 weeks were required. In non-union lesions, mixtures of autogeneous bone and granular form TCP ceramic showed bridging for 2 of 6 (50-50 mixture), autogeneous bone alone, bridging for 6 of 7, and in ceramic alone, bridging for only 3 of 8. Lemons, J. E., *Response of Combined Electrical Stimulation and Biodegradable Ceramics*, Final Report USAMRDS Contract DAMD17-75-C-5044, 1982.

In 1983 a new solid particulate TCP ($-40, +100$ mesh) was studied using 0.4 gram and 0.8 grams of TCP and 0.2/0.2 and 0.4/0.4 TCP and bone ratios within an 8 mm length rabbit tibial lesion. The TCP and autogenous bone mixture showed a slightly higher probability for clinical union compared to the TCP alone. Moreover, no statistically significant trends with respect to quantity or the presence of autogenous bone could be established.

Also in this study, the dog radii implants of TCP rod form illustrated that the results are quite variable for this type of an implant. The retained rod form showed wide range of interactions such as soft tissue reactions, fibrous incapsulations to normal bone and incorporation of the residual material. Lemons, J. E., *Applied Laboratory and Clinical Studies on Biodegradable Ceramic*, Annual Report, USAMRDS Contract DAMD17-79-C-9173, 1983.

U.S. Pat. No. 3,314,420 discloses an improved ceramic prosthetic part at least a portion of the surface area of the prosthetic part is porous to facilitate and to enable the growth of bone, muscle and fibrous tissue thereinto so as to incorporate said part into the muscular, skeletal system of the body into which the prosthetic part is implanted.

U.S. Pat. No. 3,713,860 teaches a bone substitute prepared by impregnating a porous aluminum oxide ceramic with pure methyl methacrylate monomer. The monomer is then polymerized by gama radiation. Portions of the polymer are then removed by a solution of a suitable solvent such as acetone in an ultrasonic bath where the muscle and bone attachment is desired. The finished product may then be sterilized by further radiation.

U.S. Pat. No. 3,767,437 teaches a new composition of matter for preparation of structures resembling cartilage and bone tissue with improved moisture resistant and water resistant properties. The new prosthetic structure is formed from a complex partial salt of collagen with a metal hydroxide and with an ionizable acid such as calcium hydroxide or phosphoric acid.

U.S. Pat. No. 3,892,649 discloses a method in which bone and organic matrix are simultaneously adhered by electro chemical deposition onto a metallic prosthesis. The coating of bone particles and organic binder onto the surface of the bone prosthesis is said to enhance bone growth on the prosthesis.

U.S. Pat. No. 3,919,723 teaches a prosthesis made of compacted aluminum oxide ($Al_2O_2$) ceramic which has incorporated at or near the surface a substance such a apatite or apatite-like crystals which are capable of releasing bone-stimulating ionic material such as lithium ions, boron ions, fluoride ions, sodium ions, magnesium ions, silicon ions, phosphorous ions, potassium ions, calcium ions and mixtures thereof.

U.S. Pat. No. 3,949,073 teaches a method of augmenting connective tissue by administering a solution of solubilized, purified, native, in situ polymerizable collagen to the augmentation site. The implanted solution polymerizes at the site into a stable, non-reactive fibrous mass of tissue which is rapidly colonized by host cells and subsequently vascularized.

U.S. Pat. No. 4,051,598 teaches a porous dental implant with an osteogenic catalyst at the surface layer. The osteogenic catalysts are calcium carbonate, tricalcium phosphate, calcium fluoride, tribasic calcium phosphate, monobasic calcium phosphate, calcium glycero-phosphate, calcium lacticum, sodium fluoride, total bone substance, magnesium silicate, aluminum silicate, ascorbic acid, aluminum silicate, vitamin D, vitamin A, animal dentin, dibasic calcium phosphate, calcium glucosicum, calcium hexaphosphate, caoline, zinc oxide and mixtures thereof. The coated implant of this invention is said to overcome the bond failure between the implant and the surrounding tissue.

U.S. Pat. No. 4,052,754 teaches an implant that is, at least, partially composed of a biocompatible porous material which readily promotes the ingrowth of living tissue into the implant. A porous material of carbon fibers bonded to polytetrafluroethylene is disclosed as the preferred growth promoting material.

U.S. Pat. No. 4,164,794 disclosed a prosthesis at least a portion of which is covered by a porous coating of a bioengineering thermoplastic material such as polysulfones, polyphenylenesulfide, polyacetal, thermoplastic polyesters, polycarbonates, aromatic polyamides, aromatic polyamideimides, thermoplastic polyimides, polyarylketones, polyarylethylketones, polyarylethylnitriles and aromatic polyhydroxy ethers with specific physical characteristics as disclosed in the patent. The bioengineering thermoplastic coating promotes tissue ingrowth onto the prosthetic device.

U.S. Pat. No. 4,186,448 teaches the use of a biodegradable material which is prepared from known hydroxy acids such as polylactic acid.

U.S. Pat. No. 4,187,852 teaches a cross-linked insoluble elastomeric polypentapeptide which withdraws calcium ions from blood serum, so as to result is a calcifide peptide. Use as a matrix for replacing or repairing bone is disclosed.

U.S. Pat. No. 4,222,128 teaches a composite implant material (sintered apatite and a thermoplastic or thermosetting resin) the resultant composite moderately controls compatibility of the sintered apatite material to bone and improves the strength of the sintered apatite material.

U.S. Pat. No. 4,234,972 teaches a prosthesis for cement-free bonding comprising a metal substrate coated with a biologically active glass or glass-ceramic.

U.S. Pat. No. 4,277,238 discloses an artificial implantable bone-like graph material prepared from a decalcified and defattened bone piece or tooth taken from an animal or human. The implanted graft easily assimilates with existing tissues.

U.S. Pat. No. 4,294,753 teaches the use and preparation of a bone morphogenetic protein (BMP) or BMP/calcium phosphate coprecipitate for the treatment of bone defects caused by injury, malignancy, infection and congenital absence of bone.

U.S. Pat. No. 4,309,488 discloses an implantable bone replacement material comprising a matrix material consisting of a solid core of metal and a surface region of the metal having a fine-grained inclusion of calcium phosphate ceramic material.

U.S. Pat. No. 4,314,380 teaches the preparation of an artificial bone from which the organics have been removed, then it is butrned, baked and immersed in atelocollagen solution. The atelocollagen solution provides the artificial bone with good affinity with the neighboring bone tissue and allows for firm bonding to the neighboring tissue and bone cells. Moreover, it improves the strength of the artificial bone.

It is an object of the present invention to provide treatment of major bone deficiencies, such as nonunions without the use of electrostatic or electromagnetic electrical stimulation.

A further object of the invention is to promote treatment of large bone lesions without the use of autogenous bone transplantation.

A further object of the invention is to provide treatment of bone trauma sites without the use of autogenous bone transplantation where local soft tissues have been lost.

A further object of the invention is to provide a sterile composition that may be applied at surgical bone reconstruction by filling the bone lesion site.

A further object of the invention is to provide a sterile composition, which may be delivered to the lesion site by syringe.

A further object of the invention is to provide a composition which would minimize the invasion of fibrous or other tissue and maximize opportunity for bone formation.

A further object of the invention is to provide a composition which would promote vascularization of the three-dimensional space by preventing excessive packing of the inorganic phase.

A further object of the invention is to provide a composition which will hold the inorganic substances at the bone lesion site and thereby maintain anatomical dimensions.

A further object of the invention is to provide a composition which will provide for early force transfer in order to maintain the surrounding bone and give the additive mechanical conditions for preventing the loss of length and cross-section dimensions.

A further object of the invention is to provide a composition to promote the treatment of both simple and complex bone defects.

A further object of the invention is to provide a composition which does not require the need for immunosuppressive drugs.

A further object is to provide a composition which is easy to administer and also forms an intimate bond with the surrounding tissue.

A further object is to provide a composition which does not alter bone load characteristics thereby allowing sufficient load to the ingrowth and surrounding bone to prevent resorption.

A further object of the invention is to provide a composition which provides three-dimensional form stability where glutaraldehyde cross links exists within the hydrated collagen base material which is then mixed with HAP ceramic particulate or is cross-linked with the final composition form of the hydrated collagen base materials which coat the ceramic particulate.

It is a further object of the invention to provide a composition to promote the treatment of simple and complex bone defects where the presence of a viable periosteum is not necessarily present at the time of surgical placement.

The following has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the invention. Accordingly, other objects and a fuller understanding of the invention may be had be referring to the summary of the invention and the detailed description describing the preferred embodiment in addition to the scope of the invention defined by the claims.

SUMMARY OF THE INVENTION

For the purpose of summarizing the invention, the invention may be described as a unique composition consisting of an inorganic phase and an organic phase. The composition promotes the healing or bridging of the bone lesion site. The inorganic phase comprises a biodegradable porous particulate TCP or a nonporous or microporous particulate HAP ceramic which is non-biodegradable, or a mixture of porous particulate TCP and nonporous or microporous particulate HAP ceramic. The organic phase comprises a purified hydrated collagen product and a hydrated collagen-demineralized bone product. The inorganic phase can consist entirely of either porous particulate TCP ceramic or nonporous or microporous (or mixtures thereof) particulate HAP ceramic. When biodegradability is desired, a greater amount of porous particulate TCP is utilized. When non-biodegradability is desired, a greater amount of nonporous or microporous (or mixtures thereof) particulate HAP ceramic is utilized. The relative ratio of TCP/HAP will determine the degree of biodegradability. The inorganic phase always comprises the core, the organic phase always comprises the outermost layer.

In a more specific embodiment of the invention, the nonporous or microporous (or mixtures thereof) particulate HAP ceramic and porous particulate TCP ceramic size ranges from about 10 micrometers to about 3 mm, average particle dimension. The purified hydrated collagen product provides a continuous or substantially continuous surface surface coating of the ceramic core of a thickness of about 1 to about 100 micrometers, preferably about 1 to about 5 micrometers. The hydrated collagen-demineralized bone products provide a continuous or substantially continuous thickened surface layer of about 1 to about 200 micrometers, preferably about 1 to about 50 micrometers. The sequence of the components within the organic layer, that is the outermost layer, is not critical. That is, while both elements of the organic layer must be present, either the hydrated collagen product can coat the ceramic particle or the hydrated collagen-demineralized bone product can surface or coat the ceramic particle.

Preferably, the inorganic (ceramic) phase comprises nonporous or microporous (or mixtures thereof) particulate HAP ceramic in a size range from about 10 micrometers to about 3 mm, average particle diameter dimension and porous particulate tricalcium phosphate ceramic size range from about 100 to about 250 micrometers average particle diameter dimension. The organic phase comprises a purified hydrated collagen product sufficient to provide a continuous or substantially continuous surface coating on the ceramic or organic-ceramic particle of a thickness of about 1 to about 100 micrometers preferably about 1 to about 5 micrometers; and, a hydrated collagen-demineralized bone product sufficient to provide a continuous or substantially continuous of about 1 to about 200 micrometers preferably bout 1 to about 50 micrometers on the inorganic or organic-ceramic phase. Again, it is emphasized that the relative position of the elements within the organic phase is not critical. That is, the purified hydrated collagen product may be in intimate contact with the inorganic (ceramic) phase, with the hydrated collagen-demineralized bone product covering or substantially covering the purified hydrated collagen product which in turn covers the inorganic phase. Or in the alternative, the hydrated collagen-demineralized bone product is in intimate contact with the inorganic phase with the hydrated collagen product providing a continuous or substantially continuous surface coating over said hydrated collagen-demineralized bone product and inorganic phase. Where a particular structural form may be required for the treatment of a bone lesion, additional collagen or collagen and demineralized bone product could be used in conjunction with the coated inorganic particulate.

The inventive composition may also include an effective amount of other known osteogenic property influencing material such as fluoride ions, magnesium ions, ascorbic acid, vitamin A and vitamin D and the like, or mixtures thereof. The inventive composition may also contain an effective amount of an antibiotic such as ampicillin, amoxicillin or penicillin G or V among others, or mixtures thereof.

The invention further embraces a method of treating bone deficiencies in a living mammal by using known surgical procedures in administering to the bone lesion an effective amount of the inventive composition. The inventive composition may be administered to the bone lesion which has been accessed by surgery or the inventive composition may be administered to the lesion site by a syringe injection.

The foregoing has outlined rather broadly the more pertinent and important features of the present invention in order that a detailed description that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not part from the spirit and scope of the invention as set forth in the appended claims.

DETAILED DESCRIPTION

This invention relates to a combination of inorganic ceramic and organic products to provide mechanical mixture or composite for the treatment of bone lesions.

More particularly, this invention relates to a composition for the treatment of bone lesions or bone deficiencies in live mammals comprising an inorganic phase and an organic phase wherein the inorganic phase comprises a porous particulate TCP ceramic or a nonporous or microporous particulate HAP ceramic (or mixtures of nonporous and microporous particulate HAP ceramic) or a mixture of porous particulate TCP ceramic and nonporous or microporous particulate HAP ceramic. Microporous as used herein means a pore size of less than 100 micrometers. The nonporous and microporous particulate HAP ceramic are interchangeable. That is, one can be substituted for the other. The organic phase comprises a purified hydrated (e.g. bovine) collagen product which is mixed with and forms a continuous or substantially continuous surface coating over the inorganic phase and a hydrated collagen-demineralized bone product which is mixed with and forms a continuous or substantially continuous surface coating over the purified hydrated collagen product surface coating. The sequence of the organic phase components is not critical. That is, the purified hydrated collagen product may be used to coat the hydrated collagen-demineralized bone product surface coating. However, the inorganic phase, that is the ceramic phase, must always be coated by the organic phase. The purpose in having the organic phase as the outermost phase is to maximize osteogenic inducement of the surrounding bone tissue. However, it is conceivable that the organic phase may not be the outermost phase, such as where the organic phase consists of a copolymer or higher molecular weight form produced by the polymerization of a collagen product with a demineralized bone product. Here the polymer or biocopolymer would be essentially coated by or interdispersed with the inorganic phase. However, the overall result would be expected to be the same.

The inorganic ceramics used in this invention are known: particulate biodegradable forms of beta Whitlockite tricalcium phosphate, $Ca_3(PO_4)_2$, and non-biodegradable hydroxylapatite, $Ca_{10}(PO_4)_2(OH)_2$, form ceramics (e.g., "DURAPATITE" or "CALCITITE"). U.S. Pat. No. 4,097,935 discloses a nonporous HAP. Microporous HAP is available from: Ortho Matrix, Inc., Dublin, Calif. or DuPuy Inc., MITER, Warsaw, Ind.

The granular form inorganic phase consists of two different chemical compounds with their relative amounts depending on the degree of biodegradability desired. The first will be the inorganic tricalcium phosphate ceramic fabricated as a porous particulate. The irregularly shaped particulate size fraction will range from about 10 micrometers to about 3 millimeters average particle dimension. Most often, the size fraction will be in a size range from about 100 to about 250 micrometers average diameter dimension. While a size range within the composition is not critical, it has been discovered that a range of particle sizes within the composition promotes the vascularization of the three dimensional spaces at a faster rate.

The tricalcium phosphate ceramic is spectrochemically pure beta whitlockite [$Ca_3(PO_4)_2$] fabricated as porous particulate from calcined and sintered ceramic.

The sintered product with the three-dimensional network of porosities provides the sites for attachment fixation of the organic phase. The biodegradable organic phase fills the spaces and provides a surface coating for the particulate.

The second component of the inorganic phase is nonporous or microporous hydroxylapatite ceramic. The hydroxylapatite ceramic also will be used a wide range of sizes, about 10 micrometers to about 3 millimeters, but in contrast to the tricalcium phosphate particulate, this ceramic must be nonporous (dense) or microporous (surface features) within the three-dimensional form of the particulate. This sintered product $Ca_{10}(PO_4)_6(OH)_2$ will be surface treated with a dilute hydrofluoric acid (HF) to provide limited surface irregularities for the attachment of the organic phase. This acid treatment which can be substituted by other demineralization procedures, e.g., pyruvic acid, phosphoric acid, etc. to provide three-dimensional surface irregularities for attachment of the organic component. The size and shape of the hydroxylapatite ceramic remains essentially unchanged by the acid treatment of the surface.

As to the inorganic components of the invention see: Duessins, F. C. M., The Mineral of Bone, Dentin and Tooth Enamel, Bull Soc. Chem. Belg., 89, pp. 663-669, 1980; Jarco, M., Calcium Phosphate Ceramics as Hard Tissue Prosthetics, Clin, Orth. and Rel. Res., 157, pp. 259-278, 1981. Lemons, J. E., *Applied Laboratory and Clinical Studies on Biodegradable Ceramic Annual Report*, USAMRDS, Contract DAMD17-79-C-9173, 1983 (Naphthalene generated porous TCP).

The relative amounts of porous particulate TCP ceramic and nonporous or microporous particulate HAP ceramic are determined by one skilled in the art as dictated by the degree of biodegradation desired. Where the lesion site would return to bone without retained synthetic inorganic substances or in young individuals, the biodegradable porous particulate TCP ceramic provides the inorganic filler. In contrast, where retained filler is desirable, e.g., alveolar ridge augmentation, spinal fusion, etc., the minimally biodegradable nonporous or microporous particulate HAP ceramic is used. For example, porous particulate tricalcium phosphate (TCP) and nonporous or microporous hydroxylapatite (HAP) ceramics were mixed as follows: TCP (−40+100 mesh) and 1, 2 and 3 mm sizes HAP 14 to 20 mesh at ratios of 0, 25, 50 and 100 weight percent TCP/HAP. These ratios provide a range of biodegradable ceramic mixtures.

The organic phase is a mixture of biopolymeric forms. The biopolymeric forms include: collagen products such as purified hydrated bovine collagen, demineralized bone matrix, bone matrix, bone morphogenetic protein and bone-derived growth factors: See R. L. Simpson, Collagen as a Biomaterial, Chapter II, *Biomaterials in Reconstructive Surgery*, pp. 109-118, C. V. Mosby Co., 1983; M. R. Urist, R. J. Delange and G. A. W. Finerman, Bone Cell Differentiation and Growth Factors, pp. 680-685, *Science*, 220, 1983. Demineralized bone product includes demineralized bone matrix, bone morphogenetic protein and bone-derived growth factors or mixtures thereof. The source of the biopolymeric form is not critical as long as steps, known in the art, are taken to minimize antigenicity. Collagen products are readily available. The collagen product must be in the hydrated form to be used in the composition of the invention.

The hydrated collagen-demineralized bone product is a mixture covering a range from about 1:1 to about 1:4 parts by weight. To be within the scope of the invention both the hydrated collagen product and the demineralized bone product must be present.

The ceramic to organic ratios are: about 1 to 7 parts by weight ceramic to about 1 part by weight organic. That is, the ratio of ceramic to organic covers a range from about 7:1 to about 1:1 parts by weight. The ceramic load may exceed the wetting characteristic of the organic at a 7 to 1 ratio (ceramic:organic). Ratios of 7:1 represent the highest amount of inorganic loading which can be used and where the inorganic phase is, at least, substantially covered by the organic phase. If additional organic were required to make a continuous mass, i.e., beyond the specified amount for surface coating the inorganic phase, the additional material could be collagen alone or a relative mixture of collagen and demineralized bone product.

The composition of the invention may be prepared by first mechanically mixing the purified hydrated bovine collagen product with the ceramic particulate (inorganic being added to the organic) to give a limited thickness (about 1 to about 100 micrometers) and a substantially continuous or continuous surface coating over the inorganic phase. The hydrated collagen-demineralized bone products (1 to 3 ratio by weight) are then mixed with the collagen coated ceramic particulate to provide a substantially continuous or continuous thickened surface layer (about 1 to about 200 micrometers) and a combined mass. This material is used directly in this form for defined lesions where the normal anatomy would provide the structural stability. The mixing sequence of the inorganic-organic components is not critical as long as the inorganic component is at least substantially covered by the organic component.

For example, to prepare 2 grams of a biodegradable composition of the invention using a 1:1 ceramic to organic ratio requires:

inorganic: 1 gram porous particulate TCP granular form.

organic: (a) 600 mg hydrated collagen product, (b) 400 mg of a mixture of: 100 mg hydrated collagen product—300 mg demineralized bone product. The inorganic phase is then mixed with the organic phase. In this example, the first surface coatings would be the purified hydrated bovine collagen product to provide a continuous or substantially continuous surface coating thickness of about 1 to about 5 micrometers over the ceramic TCP and the hydrated collagen-demineralized bone products to provide a continuous or substantially continuous thickness of about 1 to about 50 micrometers. Residual organic beyond that required for the surface layers provides a binder or continuous phase to provide 3-dimensional shape of form for the implant mass.

Where additional three-dimensional form stability is required from the implant material, hydrated collagen (which is then mixed with HAP ceramic particulate) or the final composition form of the hydrated collagen product base material which coat the ceramic particulate is cross-linked with glutaraldehyde. Cross-linking the final composition with glutaraldehyde is the better method since a composition according to the invention is first prepared and then cross-linked. This saves mixing steps. This cross-linked complex provides early structural stability. Furthermore, the cross-linking also provides decreased biodegration kinetics for biological resorption of the compounds. The cross-linked composition is prepared by mixing a 25% (volume) aqueous glutaraldehyde solution with the collagen product (hydrated with distilled water) at ratios of 1:100 to 1:500 parts. These mixtures with collagen and collagen-HAP (mechanically mixed) were exposed to the glutaraldehyde for 1 to 30 seconds. After washing with distilled water, these cross-linked mixtures showed physical and mechanical properties useful for implantation.

The inorganic-organic combination of the invention further provides for delivery through a premixed and pre-filled sterile syringe or similar system since the organic phase provides a lubricating and holding function upon the inorganic component(s). The collagen based materials may be lyophilized for longer shelf life and reconstituted (hydrated) prior to use.

It is believed that the organic phase provides osteogenic, osteoinductive and osteoconductive properties and the inorganic phase provides a three-dimensional porous structure into which the subsequent formation of bone occurs.

The healing of most bone lesions starts with blood infiltration, formation of a clotted mass, vascularization and maturation of the space with subsequent formation of callus to provide mechanical stabilization. Continued growth and development follows to form compact bone of similar anatomy to the original bone site. However, soft tissue components, such as fibrous granulation tissue, usually invade the physical space previously occupied by the bone. The growth and maturation of fibrous tissue is much more rapid than bone, which often leads to anatomical deficits at healed bony locations since the fibrous granulation tissue does not become bone. The synthetic bone space filling components of the invention minimize the invasion of fibrous or other tissues, thereby providing maximized opportunity for bone formation. The combination of the inorganic and organic components of the invention also prevents excessive packing of the inorganic phase thereby insuring a more complete vascularization of the three-dimensional space. Furthermore, the inorganic phase is held at the site where placed thereby maintaining anatomical dimensions. This results in early force transfer for maintaining the surrounding bone and gives the additive mechanical condition which prevents loss of length and cross-section dimensions.

While the treatment of all types of living mammalian bone lesions or bone deficiencies are contemplated by the invention, the relative size, anatomical location, type of associated conditions, general health and treatment compliance factors are critical to the success of the treatment. Treatment of such bone lesions or bone deficiencies includes, but is not limited to:

(a) central area bone lesions where viable bone surrounds the defect, e.g., cystic bone cavities where the cyst has been removed surgically.

(b) Defects in continuity either partial or complete where the periosteum is still present, e.g., traumatic injury.

(c) On-lay or augmentation procedures where the bone surface is normal and where the periosteum is still present, e.g., resorbed alvolar ridges or a depressed molar eminence due to mal-union of a fracture.

(d) On-lay procedures to establish normal contours where heavy musculature overlies the site, e.g., augmentation of the chin or long bone.

(e) Defects in continuity either partial or complete where no periosteum is present, e.g., non-unions of long bones.

(f) Augmentations and replacements where there has been a functional matrix bone loss, e.g., severe atrophy of the mandibular or maxillary bone, or sites associated with joints.

(g) Augmentations of areas wherein idiopathic bone loss of the basal skeleton is present, e.g., loss at the inferior border of the mandible or compact bone surfaces adjacent to joint spaces.

The effective amount of the inorganic-organic composition of the invention to treat a bone lesion is readily determinable by one skilled in the art considering such factors as, for example, the type of lesion or defect, the degree of biodegradability desired and the volume of the lesion or defect to be treated.

Osteogenic property related materials, such as ascorbic acid, vitamin D, vitamin A, fluoride ions, magnesium ions and other substances known in the prior art can be added to the inventive composition when this effect may be desired, e.g., a defect in continuity or a lack of periosteum at the lesion site, in an amount determinable by one skilled in the art considering the nature of the injury or defect. A fluoride ion source, e.g. sodium fluoride, is the most desirable. The initial amount of fluoride used in the composition of the invention would be the amount equivalent to that present in body fluids after oral administration of 1.1–2.2 mg of NaF per day. Furthermore, sodium fluoride may be administered orally through dietary intake or an oral dosage form.

Furthermore, antibiotics such as penicillin, amoxicillin, erythromycin ampicillin, tetracycline and the like can be added directly to the inventive composition or the infected site where need may require, e.g., traumatic septic injury, in an amount determinable by one skilled in the art considering the nature of the injury or defect, or they may be administered systemically.

The additional osteogenic antibiotic substance(s), or mixtures thereof, may be added to either the inorganic phase, organic phase or to the final composition. The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of the composition may be resorted to without departing from the spirit of the invention.

What is claimed is:

1. A composition for the treatment of bone lesions or deficiencies in live mammals comprising an effective amount of an inorganic phase and an organic phase, wherein the inorganic phase comprises an effective amount of:

porous particulate tricalcium phosphate ceramic or;

a nonporous or microporous, or mixtures thereof, particulate hydroxylapatite ceramic or;

a mixture of porous particulate tricalcium phosphate ceramic and nonporous or microporous, or mixtures thereof, particulate hydroxylapatite ceramic; and wherein the organic phase comprises an effective amount of;

purified hydrated collagen product which is placed with and forms a continuous or substantially continuous surface coating over said inorganic phase and an effective amount of hydrated collagen-demineralized bone product which is placed with and forms a continuous or substantially continuous surface coating over said purified hydrated collagen product surface coating or;

the organic phase comprises a hydrated collagen-demineralized bone product which is mixed with and forms a continuous or substantially continuous surface coating over said inorganic phase and a purified hydrated collagen product which is mixed with and forms a continuous or substantially continuous surface coating over said hydrated collagen-demineralized bone product surface coating.

2. The composition of claim 1, wherein the nonporous or microporous particulate hydroxylapatite ceramic size ranges from about 10 micrometers to about 3 millimeters, average particle diameter dimension.

3. The composition of claim 1, wherein the porous particulate tricalcium phosphate ceramic size ranges from about 10 micrometers to about 3 millimeters, average particle diameter dimension.

4. The composition of claim 3, wherein the tricalcium phosphate ceramic size ranges from about 100 to about 250 micrometers, average particle diameter dimension.

5. The composition of claim 1, wherein the purified hydrated collagen product provides a continuous or substantially continuous surface coating on the ceramic particulate of a thickness of about 1 to about 100 micrometers.

6. The composition of claim 5, wherein the coating on the ceramic particulate is of a thickness of about 1 to about 5 micrometers.

7. The composition of claim 1, wherein the hydrated collagen-demineralized bone products are mixed with the purified hydrated collagen product coated ceramic particulate to provide a thickened continuous or thickened substantially continuous surface layer of about 1 to about 200 micrometers.

8. The composition of claim 7, wherein the hydrated collagen-demineralized bone products provide a surface of about 1 to about 50 micrometers.

9. The composition of claim 1, wherein the hydrated collagen is cross-linked with glutaraldehyde.

10. The composition of claim 1, which is further cross-linked with gluteraldehyde.

11. The composition of claim 1, which is in a pre-filled, sterile, ready-to-use syringe.

12. The composition of claim 1, wherein the hydrated collagen-demineralized bone product ratio is about 1:1 to about 1:4 by weight.

13. The composition of claim 12, wherein the hydrated collagen-demineralized bone product ratio is about 1:3 by weight.

14. The composition of claim 1, wherein the ceramic to organic ratios are: about 1 to 7 parts by weight ceramic to about 1 part by weight organic.

15. The composition of claim 1, wherein the hydrated collagen product is bovine derived.

16. The composition of claim 1 which additionally contains an effective amount of an additional osteogenic material.

17. The composition of claim 16, wherein the osteogenic property related material is selected from the group consisting of: fluoride ions, magnesium ions, ascorbic acid, vitamin A and vitamin D.

18. The composition of claim 17 where the osteogenic property related material is sodium fluoride.

19. The composition of claim 1 which additionally contains an effective amount of an antibiotic.

20. A method of treating bone lesions or bone deficiencies in a living mammal comprising administering to the replacement, augmentation, defect site or bone lesion an effective amount of the composition of claim 1.

21. The method of claim 20 in which the mammal is a human.

22. The method of claim 20 in which the composition is administered to a bone lesion or bone deficiency accessed by surgery.

23. The method of claim 20 in which the composition is administered to a bone lesion or bone deficiency by a syringe.

24. The method of claim 20 in which the composition is administered to a bone lesion or bone deficiency by a syringe injection.

* * * * *